United States Patent [19]

Takahashi et al.

[11] Patent Number: 5,041,641

[45] Date of Patent: Aug. 20, 1991

[54] PENTAFLUOROPHENYL DERIVATIVES, METHODS OF PRODUCTION THEREOF, AND METHOD OF OPTICAL RESOLUTION OF CHIRAL CARBOXYLIC ACIDS

[75] Inventors: Osamu Takahashi; Keizo Furuhashi; Junko Umezawa, all of Toda, Japan

[73] Assignee: Nippon Mining Company Limited, Tokyo, Japan

[21] Appl. No.: 336,263

[22] Filed: Apr. 11, 1989

[30] Foreign Application Priority Data

Apr. 15, 1988 [JP] Japan ................................. 63-93893
Jun. 17, 1988 [JP] Japan ................................. 63-148003
Sep. 7, 1988 [JP] Japan ................................. 63-222227
Feb. 28, 1989 [JP] Japan ................................. 64-45368

[51] Int. Cl.$^5$ ............................................. C07C 53/30
[52] U.S. Cl. ................................... 562/496; 562/840; 564/182; 564/184; 558/53; 568/804; 570/127
[58] Field of Search ............... 562/496, 840; 564/188, 564/184; 568/804; 570/127; 558/53

[56] References Cited

U.S. PATENT DOCUMENTS 3,513,206  5/1979  Wall et al. ........................... 260/618

FOREIGN PATENT DOCUMENTS 0081666  6/1983  European Pat. Off. .
1256639  12/1967  Fed. Rep. of Germany .
983921  2/1965  United Kingdom .

OTHER PUBLICATIONS

CA 101(11):90422v, 1984.
CA 97(23) 197853n, 1982.
CA 97(17):144556m, 1982.
CA 97(15):127272y, 1982.
Patent Abstracts of Japan, vol. 6, No. 139, p. 134 C 116 (Jul. 28, 1982).
Chem Abstracts Registry Handbook, 1965–1971, p. 331R, No. 781-26-0, p. 427R, No. 950-67-4.
Chem. Abstracts 99(19):157528v (Nov. 7, 1983).
Chem. Abstracts 94(15):121001a (Apr. 13, 1981).
Chem. Abstracts 108(15):131541y (Apr. 11, 1988).

Primary Examiner—Paul J. Killos
Attorney, Agent, or Firm—Seidel, Gonda, Lavorgna & Monaco

[57] ABSTRACT

Pentafluorophenyl derivatives are expressed by the formula (I):

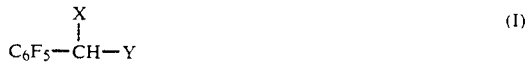

$$C_6F_5-CH-Y \quad \text{with } X \text{ on CH} \tag{I}$$

where X represents an alkyl group having from 1 to 4 carbon atoms or a halogen atom; Y represents any group of —CH$_2$OH, —COOH, —COCl, —CON$^1$R$^2$, or —OSO$_2$R$^3$; R$^1$, R$^2$ and R$^3$ represent an alkyl group which may have a substituted group, an aryl group which may have a substituted group, or a hydrogen atom except for R$^3$. However, when X to a halogen atom, Y is the aforementioned groups other than —OSO$_2$R$^3$. A racemate and/or an optical active form of the pentafluorophenyl derivatives can be used suitably as derivatizing agents for electron capture detection and optical resolution for analysis and as intermediates for medicines, agricultural chemicals, functional polymers, etc. The pentafluorophenyl derivatives are produced from pentafluorostyrene oxide.

21 Claims, No Drawings

PENTAFLUOROPHENYL DERIVATIVES, METHODS OF PRODUCTION THEREOF, AND METHOD OF OPTICAL RESOLUTION OF CHIRAL CARBOXYLIC ACIDS

BACKGROUND OF THE INVENTION

The present invention relates to novel pentafluorophenyl derivatives, methods of production thereof, and methods of optical resolution of chiral carboxylic acids.

A racemate and/or an optical active form of pentafluorophenyl derivatives in accordance with the present invention can be used suitably as derivatizing agents for electron capture detection and optical resolution for analysis and as intermediates for medicines, agricultural chemicals, functional polymers, etc.

Many fluorine-containing compounds which exhibit special physical properties and physiological activities are known. For instance, bromo(pentafluorophenyl)methane [Anal. chem., 40, 2073 (1963)] and 0-[(pentafluorophenyl)-methyl]hydroxylamine [J. chromatogr. Sci.), 13, 97 (1975)], both of which are pentafluorophenyl derivatives, can be used for sensitive analysis as electron capturing agents.

Among various pentafluorophenyl derivatives, 1-(pentafluorophenyl)ethanol is already known, and can be derived by reduction of methyl(pentafluorophenyl)ketone. In addition, an optical active one has been obtained by optical resolution or asymmetric reduction of methyl(pentafluorophenyl)ketone using optically active binaphthol. [Liebigs Ann. Chem., 1986, 2004]

However, the above-described optical resolution requires a special optical resolving agent and a complicated operation. On the other hand, the asymmetric reduction requires an expensive binaphthol as the chiral source. In addition, 2-fluoro-2-(pentafluorophenyl)ethanol and 1-(pentafluorophenyl)ethyl sulfonate are not yet known.

The present inventors found that 2,3,4,5,6-pentafluorostyrene oxide can be obtained via microbial epoxidation of 2,3,4,5,6-pentafluorostyrene (Japanese Patent Application No. 233497/1984).

The present inventors discovered novel pentafluorophenyl derivatives during the course of research concerning 2,3,4,5,6-pentafluorostyrene oxide, and found that these novel derivatives are optical active and can be suitably used particularly as derivatizing agents for electron capture detection and optical resolution for sensitive analysis, and as intermediates for medicines, agricultural chemicals, functional polymers, etc.

The present invention has been devised on the basis of this new knowledge.

SUMMARY OF THE INVENTION

Accordingly, an object of the present invention is to provide pentafluorophenyl derivatives, i.e., novel fluorine-containing compounds, methods of production thereof, and a method of optical resolution of chiral carboxylic acids.

The present invention provides pentafluorophenyl derivatives expressed by the following formula (I):

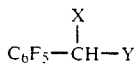
$$C_6F_5-\overset{X}{\underset{|}{C}H}-Y \quad (I)$$

(where X represents an alkyl group having from 1 to 4 carbon atoms or a halogen atom; Y represents any group of $-CH_2OH$, $-COOH$, $COCl$, $-CONR^1R^2$, or $-OSO_2R^3$; $R^1$, $R^2$ and $R^3$ represent an alkyl group which may have a substituted group, an aryl group which may have a substituted group, or a hydrogen atom except for $R^3$. However, when X is a halogen atom, Y is the aforementioned groups other than $-OSO_2R^3$).

The invention also provides optically active pentafluorophenyl derivatives expressed by the following formula (II):

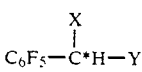
$$C_6F_5-\overset{X}{\underset{|}{C^*}H}-Y \quad (II)$$

(where C* represents asymmetric carbon; X represents an alkyl group having from 1 to 4 carbon atoms, a hydroxyl group, or a halogen atom; Y represents any group of $-CH_2OH$, $COOH$, $-COCl$, $-CONR^1 R^2$, $-OSO_2R^3$ or $-CH_2Y'$; $R^1$, $R^2$ and $R^3$ represent an alkyl group which may have a substituted group, an aryl group which may have a substituted group, or a hydrogen atom except for $R^3$; Y' represents a halogen atom. However, when X is a hydroxyl group, Y is $-CH_2X'$ group alone, while when X is a halogen atom, Y is any of the aforementioned groups other than the $CH_2Y'$ group and $-OSO_2R^3$).

The invention also proposes methods for production of pentafluorophenyl derivatives and, in particular, optically active pentafluorophenyl derivatives from pentafluorostyrene oxide.

The invention also proposes a method of optical resolution of chiral carboxylic acid using an optically active pentafluorophenyl derivative.

DESCRIPTION OF THE PREFERRED EMBODIMENTS

Pentafluorophenyl derivatives in accordance with the present invention are novel compounds expressed by the following formula (I):

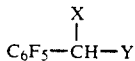
$$C_6F_5-\overset{X}{\underset{|}{C}H}-Y \quad (I)$$

(where X represents an alkyl group having from 1 to 4 carbon atoms or a halogen atom; Y represents any group of $-CH_2OH$, $-COOH$, $-COCl$, $-CONR^1R^2$, or $-OSO_2R^3$; and $r^1$, $R^2$ and $R^3$ represent an alkyl group which may have a substituted group, an aryl group which may have a substituted group, or a hydrogen atom except for $R^3$. However, when x is a halogen atom, Y is the aforementioned groups other than $-OSO_2R^3$).

Optically active pentafluorophenyl derivatives in accordance with the present invention are novel optically active compounds expressed by the following formula (II):

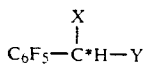 (II)

(where C* represents asymmetric carbon; X represents an alkyl group having from 1 to 4 carbon atoms, a hydroxyl group, or a halogen atom; Y represents any group of —CH₂OH, —COOH, —COCl, —CONR¹R², —OSO₂R³ or —CH₂Y'; R¹, R² and R³ represent an alkyl group which may have a substituted group, an aryl group which may have a substituted group, or a hydrogen atom except for R³; and Y' represents a halogen atom. However, when X is a hydroxyl group, Y is —CH₂Y' group alone, while when X is halogen, Y is any of the aforementioned groups other than the CH₂Y' group and —OSO₂R³).

More specifically, 2-(pentafluorophenyl)-1-alkanols expressed by the following formula (III):

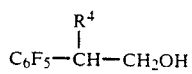 (III)

(where R⁴ represents an alkyl group having from 1 to 4 carbon atoms) can be produced by reacting 2,3,4,5,6-pentafluorostyrene oxide with trialkylaluminum having an alkyl group of from 1 to 4 carbon atoms (from 1 to 8 equivalents preferably from 1 to 2 equivalents).

An aliphatic hydrocarbon solvent such as hexane, an aromatic hydrocarbon solvent such as toluene, a halogenated solvent such as dichloromethane, or a mixed solvent thereof may be used. The reaction temperature is set at −50° to 100° C. The desired 2-(pentafluorophenyl)-1-alkanols are obtained by pouring the reaction mixture into a diluted hydrochloric acid or the like, extracting with an organic solvent such as ether, and then distilling the extract under reduced pressure.

Optically active 2-(pentafluorophenyl)-1-alkanols expressed by the following formula (IV):

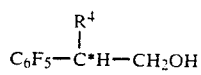 (IV)

(where C* represents asymmetric carbon; R⁴ represents an alkyl group having from 1 to 4 carbon atoms) can similarly be produced by using optically active 2,3,4,5,6-pentafluorostyrene oxide as the starting material.

As an example of the alkanols expressed by the aforementioned formula (IV), the physical properties of (+)-2-(pentafluorophenyl)-1-propanol are shown as follows.

Boiling point: 110° C./20 mmHg
Specific rotation [α]$_D^{25}$: +17.1° (c 5.1, CHCl₃)
¹H NMR(CDCl₃): 1.33(d, 7.2Hz, 3H), 1.87(S, OH), 3.1–3.7 (m, 1H), 3.82(d, 7.5 Hz, 2H)
¹⁹F NMR(CDCl₃, ext. CF₃CO₂H): 66.8(m, 2F), 81.3(t, 22 Hz, 1F), 86.8(m, 2F)
IR (Film method, cm⁻¹): 3300, 1515, 1495, 1105, 1055, 1030, 965

2-(pentafluorophenyl)alkanoic acids expressed by the following formula (V):

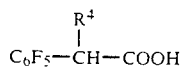 (V)

(where R⁴ represents an alkyl group having from 1 to 4 carbon atoms) can be produced by oxidation 2-(pentafluorophenyl)-1-alkanols expressed by the aforementioned formula (III) using an oxidizing agent, including a permanganate such as potassium permanganate, or a chromic acid (from 1 to 2 equivalents).

The solvent used at this juncture is preferably diluted sulfuric acid, acetone, or a mixed solvent thereof, and the reaction temperature is set to from 0° to 30° C.

The reaction mixture thus obtained is extracted with an organic solvent such as ethyl acetate after excess oxidizing agent has been reduced using an aqueous sodium bisulfite solution or the like. Furthermore, an organic layer is extracted with an aqueous alkaline solution, the aqueous layer is acidified and extracted with an organic solvent such as ethyl acetate or the like. The solvent is distilled out under reduced pressure, to give 2-(pentafluorophenyl)alkanoic acid.

Optically active 2-(pentafluorophenyl)alkanoic acids expressed by the formula (VI):

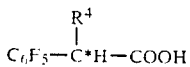 (VI)

(where C* represents asymmetric carbon; R⁴ represents an alkyl group having from 1 to 4 carbon atoms) can be similarly produced by using optically active 2-(pentafluorophenyl)-1-alkanols expressed by the aforementioned formula (IV) as starting materials.

As an example of the alkanoic acids expressed by the aforementioned formula (VI), the physical properties of (−)-2-(pentafluorophenyl)propionic acid are shown as follows.

Boiling point: 100° C./0.7 mmHg
Melting point: 57° C.
Specific rotation [α]$_D^{25}$: −26.7° (c 1.0, CHCl₃)
¹H NMR(CDCl₃): 1.55(d, 7.2 Hz, 3H), 4.13(q, 7.2 Hz, 1H), 11.0(b, OH)
¹⁹F NMR(CDCl₃, ext. CF₃CO₂H): 66.5(m, 2F), 79.4(t, 20 Hz, 1F), 85.9(m, 2F)
IR (KBr method, cm⁻¹): 3000, 1715, 1520, 1500, 965, 925

In addition, 2-(pentafluorophenyl)alkanoyl chlorides expressed by the following formula (VII):

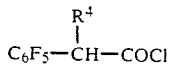 (VII)

(where R⁴ represents an alkyl group having from 1 to 4 carbon atoms) can be produced by reacting 2-(pentafluorophenyl)-alkanoic acids of the aforementioned formula (V) with a chlorinating agent such as thionyl chloride, phosphorus trichloride, phosphorus pentachloride, phthaloyl chloride, or the like(from 1 to 5 equivalents).

In this reaction, a hydrocarbon or halogenated hydrocarbon solvent, or no solvent may be used. The reaction temperature is set to from 20° to 100° C., preferably from 60° to 100° C. The disired 2-(pentafluorophenyl)alkanoyl chlorides can be obtained by distillation of the reaction mixture under reduced pressure.

Optically active 2-(pentafluorophenyl)alkanoyl chlorides expressed by the following formula (VIII):

(VIII)

(where C* represents asymmetric carbon; R⁴ represents an alkyl group having from 1 to 4 carbon atoms) can be similarly produced by using optically active 2-(pentafluorophenyl)alkanoic acids of the aforementioned formula (VI) as starting materials.

As an example of the chlorides expressed by the aforementioned formula (VIII), the physical properties of (−)-2-(pentafluorophenyl)propionyl chloride are shown as follows.

Boiling point: 60° C./2.5 mmHg
Specific rotation [α]$_D^{25}$: −27.8° (c 1.0, CHCl₃)
¹H NMR(CDCl₃): 1.64(d, 7.2 Hz, 3H), 4.45(q, 7.2 Hz, 1H)
¹⁹H NMR(CDCl₃, ext. CF₃CO₂H) 66.0(m, 2F), 77.3(t, 23 Hz, 1F) 84.8(m, 2F)
IR (Film method, cm⁻¹): 2940, 1790, 1655

2-(pentafluorophenyl)alkanamides expressed by the following formula (X):

(X)

(where R¹ and R² represent an alkyl group which may have a substituted group, an aryl group which may have a substituted group, or a hydrogen atom; R⁴ represents a alkyl group having from 1 to 4 carbon atoms) can be produced by reacting 2-(pentafluorophenyl)alkanoyl chlorides of the aforementioned formula (VII) with amines expressed by the formula (IX):

NHR¹R²      (IX)

(where R¹ and R² represent an alkyl group which may have a substituted group, an aryl group which may have a substituted group, or a hydrogen atom).

At this juncture, it is preferred that excess amines (from 2 to 20 equivalents) are used or that a base such as pyridine, triethylamine, sodium hydroxide, or the like (from 1 to 10 equivalents) is used together with the amines (from 1 to 2 equivalents). Water or halogenated solvent such as dichloromethane is used as the solvent and the reaction temperature is set to from 0° to 30° C. The desired 2-(pentafluorophenyl)alkanamides are obtained by pouring the reaction mixture into water or diluted chloric acid and extraction with an organic solvent such as ether or ethyl acetate.

Optically active 2-(pentafluorophenyl)alkanamides expressed by the following formula (XI):

(XI)

(where C* represents asymmetric carbon; R¹ and R² represent an alkyl group which may have a substituted group, an aryl group which may have a substituted group, or a hydrogen atom; R⁴ represents an alkyl group having from 1 to 4 carbon atoms) can be similarly produced by using optically active 2-(pentafluorophenyl)alkanoyl chlorides of the aforementioned formula (VIII) as the starting materials.

As an example of the amides expressed by the aforementioned formula (XI), the physical properties of (−)-2-(pentafluorophenyl)propanamide are shown as follows.

Melting point: 123° C.
Specific rotation [α]$_D^{25}$: −26.6° (c 1.0, CHCl₃)
¹H NMR(CDCl₃): 1.55(d, 7.2 Hz, 3H), 4.02(q, 7.2 Hz, 1H), 5.2–6.8(b, NH)
¹⁹F NMR(CDCl₃, ext. CF₃CO₂H) 66.3(m, 2F), 79.7(t, 19 Hz, 1F), 85.9(m, 2F)
IR (KBr method, cm⁻¹): 3470, 3340, 3180, 1685, 1525, 1500, 960, 920

Pentafluorophenyl derivatives expressed by the following formula (XII):

(XII)

(where R⁵ and R⁶ represent a hydrogen atom or a hydroxyl group and are different from each other, and C* represents asymmetric carbon) can be produced by reacting 2,3,4,5,6-pentafluorostyrene oxide with a compound expressed by the formula: Li₂MX₄ (where M represents a copper or nickel atom, and X represents a halogen atom). They can be obtained in optically active form when optically active 2,3,4,5,6-pentafluorostyrene oxide is used as the starting material.

As compounds of the aforementioned formula (XII), it is possible to cite (R)-(−)-2-bromo-1-(pentafluorophenyl)-ethanol, (S)-(+)-2-bromo-1-(pentafluorophenyl)ethanol, (+)-2-bromo-2-(pentafluorophenyl)ethanol, (−)-2-bromo-2-(pentafluorophenyl)ethanol, (R)-(−)-2-chloro-1-(pentafluorophenyl)ethanol, (S)-(+)-2-chloro-1-(pentafluorophenyl)ethanol, (+)-2-chloro-2-(pentafluorophenyl)-ethanol, (−)-2-chloro-2-(pentafluorophenyl)ethanol, or the like.

The physical properties of typical compounds among these compounds will be shown below.

(R)-(−)-2-bromo-1-(pentafluorophenyl)ethanol

① ¹H NMR (CDCl₃): 3.24 (OH), 3.76 (2H, m), 5.31 (1H, t, 7.2 Hz)
② ¹⁹F NMR (CDCl₃, external reference CF₃CO₂H): 66.7 (2F), 77.3 (1F, t, 18 Hz), 85.4 (2F)
③ IR (thin film, cm⁻¹): 3700, 1626, 1494, 1300, 1118, 986, 930, 860
④ MS (m/z): 292 (M+2), 290 (M), 197 (M—CH₂Br)
⑤ [α]$_D^{25}$: −1.8° (c 2.0, CHCl₃) (+)-2-bromo-2-(pentafluorophenyl)ethanol
① 1H NMR (CDCl₃): 3.12 (OH), 4.17 (2H, m), 5.25 (1H, t, 7.2 Hz)
② ¹⁹F NMR (CDCl₃, external reference CF₃CO₂H): 64.1 (2F), 76.7 (1F, t, 18 Hz), 85.2 (2F)
③ IR (thin film, cm⁻¹): 3700, 1650, 1496, 1424, 1300, 1128, 1030, 900
④ MS: 292 (M+2), 290 (M), 211 (M−Br)
⑤ [α]$_D^{25}$: +24.9° (c 2.2, CHCl₃)

(R)-(−)-2-chloro-1-(pentafluorophenyl)ethanol

① ¹H NMR (CDCl₃): 2.94 (OH), 3.89 (2H, m), 5.31 (1H, m)
② ¹⁹F NMR (CDCl₃, external reference CF₃CO₂H): 66.6 (2F), 77.2 (1F, t, 20 Hz), 85.2 (2F)

③ IR (CHCl₃, cm⁻¹): 3580, 3350, 1650, 1495, 1120, 990
④ MS: 248 (M+2), 246 (M), 197 (M—CH₂Cl)
⑤ [α]$_D^{25}$: −2.5° (c 2.7, CHCl₃)

(+) -2-chloro-2-(pentafluorophenyl)ethanol

① ¹H NMR (CDCl₃) 3.20 (OH), 4.12 (2H, m), 5.27 (1H, t, 7.2 Hz)
② ¹⁹F NMR (CDCl₃, external reference CF₃Co₂H): 64.5 (2F), 76.6 (1F, t, 18 Hz), 85.3 (2F)
③ IR (CHCl₃, cm⁻¹): 3580, 3380, 1652, 1494, 1126, 1040, 992, 966
④ MS: 248 (M+2), 246 (M), 215 (M—CH₂OH)
⑤ [α]$_D^{25}$: +30.6° (c 0.6, CHCl₃)

The compounds of the aforementioned formula (XII) can be produced from 2,3,4,5,6-pentafluorostyrene oxide by the following procedure. To a solution of 2,3,4,5,6-pentafluorostyrene oxide in an organic solvent such as tetrahydrofuran, is added an organic solution of Li₂MX₄ such as Li₂CuCl₄, Li₂NiCl₄, Li₂CuBR₄, or Li₂NiBr₄ to react. Incidentally, this Li₂MX₄ can be prepared by mixing copper halide (CuX₂) or nickel halide (NiX₂) and lithium halide (LiX) with a molar ratio of 1/2 in an organic solvent.

In this reaction, from 1 to 3 mol of Li₂MX₄ is suitably used for 1 mol of the epoxide. The reaction temperature can be set in a wide range from −80° to 70° C, but the range of from −10° to 30° C. is preferable.

Meanwhile, in this reaction, a mixture of compounds expressed by the following formulae (XIII) and (XIIIa):

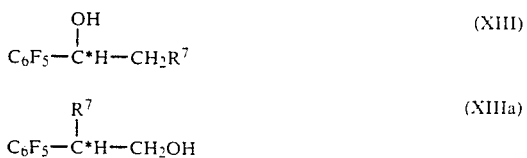

(where R⁷ represents a halogen atom, and C* represents asymmetric carbon) is obtained. They can be separated relatively easily by such means as silica gel column chromatography.

1-(Pentafluorophenyl)ethanols can be produced by reacting 2-halo-1-(pentafluorophenyl)ethanols of the aforementioned formula (XIII) with an organotin hydride expressed by the formula: R₄₋ₙSnHₙ (where R is a mutually identical or different alkyl group having from 1 to 7 carbon numbers, and n is 1 or 2).

It should be noted that 1-(pentafluorophenyl)ethanol can be produced by using a mixture of the compounds of the formulae XIII) and XIIIa). In this case, removal of 2-(pentafluorophenyl)ethanol by-produced is easier than the separation of the compounds of the formulae (XIII) and (XIIIa). Hence, this procedure is preferable.

In the production of 1-(pentafluorophenyl)ethanol, R⁷ in the formulae (XIII) is not particularly restricted. However, in view of the ease of reaction and the availability of the material, chlorine or bromine is preferable, and bromine is more preferable.

Meanwhile, as an organotin hydride expressed by the formula: R₄₋ₙSnHₙ, it is possible to cite trimethyltin hydride, triethyltin hydride, tributyltin hydride, triphenyltin hydride, dibutyltin hydride, diphenyltin hydlide or the like.

The reaction between the compound of the formula (XIII) and an organotin hydride may be carried out with no solvent, a hydrocarbon solvent, such as hexane or benzene, or an ether solvent, such as diethyl ether. In addition, if a radical initiator such as α, α'-azobisisobutyronitrile is added to the reaction system as a reaction initiator, it is possible to allow reaction to proceed efficiently. Optically active 1-(pentafluorophenyl)ethanol can be produced by using optically active compounds of the formula (XIII) as the starting material.

In addition, 1-(pentafluorophenyl)ethyl sulfonate expressed by the following formula (XV):

(where R³ represents an alkyl group which may have a substituted group or an aryl group which may have a substituted group) can be produced by reacting 1-(pentafluorophenyl)ethanol with sulfonyl chloride expressed by the following formula (XIV):

(where R³ represents an alkyl group which may have a substituted group or an aryl group which may have a substituted group).

Although R³ in the compounds of the aforementioned formulae (XV) and (XIV) is not particularly restricted, methyl, p-tolyl or the like is preferable in view of the availability of the material.

As the compounds expressed by the aforementioned formula (XV), it is possible to cite 1-(pentafluorophenyl)-ethyl methanesulfonate, 1-(pentafluorophenyl)ethyl ethanesulfonate, 1-(pentafluorophenyl)ethyl 1-methylethanesulfonate, 1-(pentafluorophenyl)ethyl butanesulfonate, 1-(pentafluorophenyl)ethyl cyclohexanesulfonate, 1-(pentafluorophenyl)ethyl phenylmethanesulfonate, 1-(pentafluorophenyl)ethyl benzenesulfonate, 1-(pentafluorophenyl)ethyl p-toluenesulfonate, 1-(pentafluorophenyl)ethyl chloromethanesulfonate, 1-(pentafluorophenyl)ethyl p-nitrophenylmethanesulfonate, 1-(pentafluorophenyl)ethyl o-nitrobenzenesulfonate, and so forth.

With respect to typical compounds of the aforementioned formula (XV), their physiochemical properties will be described below.

(S)-(−)-1-(pentafluorophenyl)ethyl methanesulfonate

① Boiling point: 130°-140° C./2.5 mmHg (Kugelrohr)
② ¹NMR (CDCl₃): 1.80 (3H, d, 7.1 Hz), 2.99 (3H, s), 6.06 (1H, q, 7.1 Hz)
③ [α]$_D^{25}$: −53.3° (c 1.2, CHCl₃)

The compounds expressed by the aforementioned formula (XV) can be produced by reacting 1-(pentafluorophenyl)ethanol with the sulfonyl chlorides expressed by the aforementioned formula (XIV).

In addition, if an optical active 1-(pentafluorophenyl)-ethanol is used as a starting material, it is possible to produce optically active 1-(pentafluorophenyl)ethyl sulfonate expressed by the following formula (XVI):

$$\begin{array}{c} \text{CH}_3 \quad \text{O} \\ | \quad \quad \| \\ \text{C}_6\text{F}_5-\text{C*H}-\text{O}-\text{S}-\text{R}^3 \\ \| \\ \text{O} \end{array} \quad \text{(XVI)}$$

(where C* represents asymmetric carbon, and $R^3$ represents an alkyl group which may have a substituted group or an aryl group which may have a substituted group).

As sulfonyl chlorides expressed by the aforementioned formula (XIV), it is possible to use, for instance, methanesulfonyl chloride, ethanesulfonyl chloride, 1-methylethanesulfonyl chloride, butanesulfonyl chloride, cyclohexanesulfonyl chloride, phenylmethanesulfonyl chloride, benzenesulfonyl chloride, p-toluenesulfonyl chloride, chloromethanesulfonyl chloride, p-nitrophenylmethanesulfonyl chloride, o-nitrobenzenesulfonyl chloride, or the like.

In this reaction, it is particularly preferable to use a neutralizing agent such as pyridine, 2,6-lutidine, 4-(N,N-dimethylamino)pyridine, triethylamine, tributylamine, or the like.

The aforementioned reaction takes place by addition of sulfonyl chloride and, if desired, a neutralizing agent to 1-(pentafluorophenyl)ethanol. This reaction is preferable to take place in the presence of an organic solvent such as ether, dichloromethane, chloroform, or the like. Ordinarily, the compound of the aforementioned formula (XIV) and the neutralizing agent may be used from 1 to 5 equivalents with respect to 1-(pentafluorophenyl)ethanol, and are used in excessive amounts when the reactivity is low. Furthermore, when an amine is used as a neutralizing agent, the amine may be used as a reaction solvent. The reaction temperature is selected in the range of from $-120°$ to $100°$ C., as necessary.

Upon completion of reaction, an aqueous solution of diluted acid or alkali is added into the reaction mixture, and a series of usual operations such as extraction, washing, drying, concentration, etc. affords the compound expressed by the formula (XV).

A description will now be given of a method of optical resolution of chiral carboxylic acids by using optically active 1-(pentafluorophenyl)ethyl sulfonate expressed by the aforementioned formula (XVI).

Although the chiral carboxylic acids to which the present invention can be applied is not particularly restricted, the present invention is suitably applied particularly to those carboxylic acids in which C2 is an asymmetric center including 2-phenylpropionic acid, 2-(substituted phenyl)propionic acid, 2-methyloctanoic acid, and the like.

In the present invention, if the aforementioned chiral carboxylic acid is reacted with optically active 1-(pentafluorophenyl)ethyl sulfonate expressed by the aforementioned formula (XVI) and tetraalkylammonium hydroxide expressed by the following formula (XVIII):

$$R'_4\text{NOH} \quad \text{(XVIII)}$$

(where R' represents an identical or different alkyl group) in a two-layer system of water and an organic solvent, a pair of diasteromers of 1-(pentafluorophenyl)ethyl ester is produced and extracted in the organic solvent. If this organic layer is subjected to chromatography, the aforementioned diastereomers are separated.

Although $R'_4$ in the aforementioned formula (XVIII) is not particularly restricted, tetrabutylammonium hydroxide is preferable in view of its availability. As this compound, it is possible to use one which is produced in situ using tetrabutylammonium hydrogen sulfite or the like and alkali hydroxide.

The amount of the optical active 1-(pentafluorophenyl)ethyl sulfonate and tetraalkylammonium hydroxide used is selected in the range of from 1 to 10000 equivalents with respect to the chiral carboxylic acid, as required, depending on the amount of chiral carboxylic acid, their concentrations in water, reactivity, and so forth. In addition, the organic solvent to  used is not particularly restricted as it is capable of b  .g separated from water in the form of a layer. For example dichloromethane, chloroform, benzene, toluene, or similar solvents are suitably used.

2-fluoro-2-(pentafluorophenyl)ethanol expressed by the following formula (XVII):

$$\begin{array}{c} \text{F} \\ | \\ \text{C}_6\text{F}_5-\text{CH}-\text{CH}_2\text{OH} \end{array} \quad \text{(XVII)}$$

can be produced by reacting 2,3,4,5,6-pentafluorostyrene oxide with an amine-hydrogen fluoride complex.

In addition, optically active 2-fluoro-2-(pentafluorophenyl)ethanol can be similarly produced by using an optical active 2,3,4,5,6-pentafluorostyrene oxide as a starting material.

Physical properties of 2-fluoro-2-(pentafluorophenyl)-ethanol are as follows:

IR (KBr) ($cm^{-1}$): 3350, 1660, 1500, 1460, 1300, 1130, 1080, 1040, 1000

$^{19}$F NMR (CDCl$_3$, external reference CF$_3$COOH) (ppm): 65.5 (2F), 76.0 (1F), 85.1 (2F), 114.7 (1F)

MS: 230 (M), 199 (M—CH$_2$OH)

In addition, the amine-hydrogen fluoride complex can be prepared easily by dropping anhydrous hydrogen fluoride into an amine and mixing them. The ratio of the amine and hydrogen fluoride in this complex can be set easily by adjusting the mixing ratio of these compounds. Even the amine-hydrogen fluoride complex has been prepared, the ratio can be changed readily by readdition of the amine or hydrogen fluoride. In addition, this complex can also be prepared by mixing amine and hydrofluoric acid followed by removal of water under reduced pressure.

As the amine of the above-described complex, it is possible to cite propylamine, isopropylamine, butylamine, isobutylamine, sec-butylamine, tert-butylamine, diethylamine, dipropylamine, diisopropylamine, dibutylamine, di-secbutylamine, triethylamine, tripropylamine, tributylamine, hexylamine, dihexylamine, trihexylamine, heptylamine, octylamine, tert-octylamine, dioctylamine, decylamine, octadecylamine, pyridine, etc.

This reaction may be carried out with no solvent or in an organic solvent such as chloroform, methylene chloride, carbon tetrachloride, diethyl ether, ethyl acetate, acetone, hexane, benzene, acetonitrile, or the like.

This reaction can be allowed to take place in wide temperature range of $-20°$ to $130°$ C., however, an optimum reaction temperature should be determined on the basis of the type of amine-hydrogen fluoride complex and the type of solvent.

In addition, the reaction time may be selected appropriately within the range of 0.5 to 120 hours in correspondence with the reaction temperature.

Furthermore, the amount of amine-hydrogen fluoride complex used is selected in the range of from 0.5 to 10 equivalents in terms of the amount of amine with respect to pentafluorostyrene oxide.

After the above-described reaction is completed, 2-fluoro-2-(pentafluorophenyl)ethanol is isolated through the usual treatment such as extraction, distillation, column chromatography, etc.

The above-described 2-fluoro-2-(pentafluorophenyl)ethanol, including optically active one, can be reacted with various compounds by using reactivity of hydroxyl group to give medicines, agricultural chemicals, or liquid crystal compounds that exhibit novel functions.

A detailed description of the present invention will be given hereafter on the basis of examples.

$^1$H NMR (Varian EM-360), $^{19}$F NMR (JEOL FX-90Q and GSX-270), IR (Shimadzu-435) and MS(JEOL DX300) were used in the identification of pentafluorophenyl derivatives.

Example 1

A solution of 10.5 g of (+)-2,3,4,5,6-pentafluorostyrene oxide (over 95%ee) in 50 ml of dichloromethane was added dropwise to 100 ml of a 1.0M solution of trimethylaluminum in hexane, and was reacted for 40 hours at room temperature. This reaction mixture was poured into 100 ml of 1N hydrochloric acid. After the aqueous layer was extracted with ether, the total organic solution was dried over magnesium sulfate. The solvent was distilled out under reduced pressure, and the subsequent distillation under reduced pressure gave 10.6 g of (+)-2-(pentafluorophenyl)-1-propanol having the aforementioned physical properties.

Reference Example 1

To a solution of 113 mg of (+)-2-(pentafluorophenyl)-1-propanol obtained in Example 1 in 0.5 ml of pyridine, was added 126 mg of (S)-(−)-methoxy(trifluoromethyl)phenylacetate chloride to react for 1 hour at room temperature.

This reaction mixture, after being diluted with ether, was washed consecutively with 1N hydrochloric acid, an aqueous solution of 5% sodium carbonate, and water. After this ether solution was dried over magnesium sulfate, the solvent was distilled off under reduced pressure. When $^{19}$F NMR (solvent: CDCl$_3$, external reference: CF$_3$CO$_2$H) of the product was measured, singlets were observed at 4.37 ppm and 3.99 ppm.

From a ratio of integration thereof, the optical purity of (+)-2-(pentafluorophenyl)-1-propanol obtained in Example 1 was determined to be 63%ee.

Example 2

To a 10 ml of ice-cooled 1M solution of trimethylaluminum in hexane, was added dropwise a solution of 1.05 g of (+)-2,3,4,5,6-pentafluorostyrene oxide (over 95%ee) in 5 ml of hexane, to react for five hours at 0° C and for another one hour at room temperature. The similar work-up to Example 1 gave 1.10 g of (+)-2-(pentafluorophenyl)-1-propanol. The specific rotation was compared with that of Example 1, and the optical purity was determined to be 15%ee.

Example 3

To a solution of 1.05 g of (+)-2,3,4,5,6-pentafluorostyrene oxide (over 95%ee) in 10 ml of dichloromethane, was added a 6 ml of 1.0M solution of trimethylalumimum in hexane, to react for one hour at 40° C. The similar work-up to Example 1 gave 1.10 g of (+)-2-(pentafluorophenyl)-1-propanol. The specific rotation was compared with that of Example 1, and the optical purity was determined to be 69%ee.

Example 4

To a vigorously stirred mixture of 9.05 g of (+)-2-(pentafluorophenyl)-1-propanol, 25 ml of acetone and 100 ml of 3N sulfuric acid, was added portionwise 12.6 g of potassium permanganate over six hours. After the mixture was further stirred for 30 minutes, this reaction mixture was poured into 150 ml of an aqueous solution of 15% sodium bisulfite, and extracted with ethyl acetate. The organic layer was extracted with an aqueous solution of 5% potassium carbonate. This aqueous layer was acidified with concentrated hydrochloric acid followed by extraction with ethyl acetate. This extracted solution was then dried over magnesium sulfate. The solvent was distilled off under reduced pressure, and the subsequent distillation under reduced pressure gave 8.23 g of (−)-2-(pentafluorophenyl)propionic acid having the aforementioned physical properties.

Example 5

A mixture of 4.8 ml of thionyl chloride and 8.10 g of (−)-2-(pentafluorophenyl)propionic acid obtained in Example 4 was stirred for 10 hours at 80° C. Excess thionyl chloride was distilled off under reduced pressure, and the subsequent distillation under reduced pressure gave 6.61 g of (−)-2-(pentafluorophenyl)propionyl chloride having the aforementioned physical properties.

Reference Example 2

To a solution of 12 mg of L-α-phenylethylamine and 0.1 ml of triethylamine in 1 ml of dichloromethane, was added 26 mg of (−)-2-(pentafluorophenyl)propionyl chloride obtained in Example 5 to react for one hour at room temperature. When the resulted amide was analyzed by gas chromatography (OV 101, 50m, 80°-240° C.), two peaks corresponding to diastereomers were observed. From a ratio of integration thereof, the optical purity of (−)-2-(pentafluorophenyl)propionyl chloride obtained in Example 5 was determined to be 63%.

Example 6

To an ice-cooled 10 ml of concentrated aqueous ammonia, was added dropwise 2.5 g of (−)-2-(pentafluorophenyl)-propanoyl chloride obtained in Example 5. After stirring for 30 minutes at room temperature, the reaction mixture was diluted with water, extracted with ethyl acetate and then dried over magnesium sulfate. The solvent was distilled off under reduced pressure, and the subsequent recrystallization from a hexane-ether mixed solvent gave 1.92 g of (−)-2-(pentafluorophenyl)propaneamide as colorless needles having the aforementioned physical properties.

Example 7

To an ice-cooled solution of 10.51 g of (R)-(+)-2,3,4,5,6-pentafluorostyrene oxide in 100 ml of tetrahydrofuran, was added dropwise a solution of Li$_2$CuBr$_4$, which was prepared by adding 16.75 g of cupric bromide to a suspension of 13.03 g of lithium bromide suspended in 150 ml of tetrahydrofuran. After completion of addition, the solution was stirred for one hour in an ice bath, and for another two hours at room temperature. The resulted reaction mixture was poured into a 0.05 mol phosphate buffer, and was extracted with ether. The resultant extract was dried over magnesium sulfate, and the solvent was distilled off under reduced pressure, thereby obtaining 11.92 g of (R)-(−)-2-bromo-1-(pentafluorophenyl)ethanol containing 20% of (+)-2-bromo-2-(pentafluorophenyl)ethanol. This was subjected to isolation by silica gel column chromatography, thereby obtaining (R)-(−)-2-bromo-1-(pentafluorophenyl)ethanol and (+)-2-bromo-2-(pentafluorophenyl)ethanol respectively possessing the aforementioned physical properties.

Example 8

To an ice-cooled solution of 10.51 g of (R)-(+)-2,3,4,5,6-pentafluorostyrene oxide was dissolved in 100 ml of tetrahydrofuran, was added dropwise a solution of $Li_2CuCl_4$, which was prepared by adding 10.08 g of cupric chloride to a suspension of 6.36 g of lithium chloride in 150 ml of tetrahydrofuran. After completion of addition, the solution was stirred for 20 hours at room temperature. The resulted reaction mixture was poured into a 0.05 mol phosphate buffer, and was extracted with ether. The resulted extract was dried over magnesium sulfate, and the solvent was distilled off under reduced pressure, thereby obtaining 12.00 g of (R)-(−)-2-chloro-1-(pentafluorophenyl)ethanol containing 20% of (+)-2-chloro-2-(pentafluorophenyl)ethanol. This was subjected to isolation by silica gel column chromatography, thereby obtaining (R)-(−)-2-chloro-1-(pentafluorophenyl)-ethanol and (+)-2-chloro-2-(pentafluorophenyl)ethanol respectively possessing the aforementioned physical properties.

Example 9

To an ice-cooled solution of 1.05 g of (R)-(+)-2,3,4,5,6-pentafluorostyrene oxide in 10 ml of tetrahydrofuran, was added dropwise a solution of $Li_2NiBr_4$, which was prepared by adding 2.19 g of nickel (II) bromide to a suspension of 1.74 g of lithium bromide in 20 ml of tetrahydrofuran. After completion of addition, the solution was stirred for 15 hours at room temperature. The resulted reaction mixture was poured into a 0.05 mol phosphate buffer, and was extracted with ether. The resultant extract was dried over magnesium sulfate, and the solvent was distilled off under reduced pressure, thereby obtaining 1.02 g of (R)-(−)-2-bromo-1-(pentafluorophenyl)ethanol containing 15% of (+)-2-bromo-2-(pentafluorophenyl)ethanol.

Example 10

To a solution of 11.26 g of (R)-(−)-2-bromo-1-(pentafluorophenyl)ethanol containing 20% of 2-bromo-2-(pentafluorophenyl)ethanol obtained in Example 7 in 50 ml of hexane, was added 11.4 ml of tributyltin hydride at room temperature. After stirring for eight hours at 60° C., the reaction mixture was concentrated under reduced pressure, purified by silica gel column chromatography and distilled under reduced pressure to give 4.0 g of (S)-(−)-1-(pentafluorophenyl)ethanol having the following physical properties.

$^1H$ NMR($CDCl_3$) 1.63 (3H, d, 6.8 Hz), 2.43 (1H, bs), 5.24 (1H, q, 6.8 Hz)

$[\alpha]_D^{25}$: −8.1° (c 2.7, pentane)

Example 11

A mixture of 1.23 g of (R)-(−)-2-chloro-1-(pentafluorophenyl)ethanol obtained in Example 8, 1.60 ml of tributyltin hydride, and 16 mg of AIBN was stirred for eight hours at 80° C. After completion of reaction, the reaction mixture was purified by silica gel column chromatography to give 0.7 g of (S)-(−)-1-(pentafluorophenyl)-ethanol.

Example 12

To an ice-cooled suspension of 0.76 g of lithium aluminum hydride in 15 ml of dry ether, was added 6.88 g of diphenyltin dichloride dissolved in 20 ml of dry ether. After stirring for 30 minutes, 20 ml of water was added to the resulted reaction mixture, and the ether layer was washed with icy water and dried over calcium chloride. The subsequent concentration under reduced pressure gave diphenyltin hydride.

To this was added 2.47 g of (R)-(−)-2-chloro-1-(pentafluorophenyl)ethanol obtained in the method of Example 8, and was stirred for one hour at 60° C. to allow reaction to take place. After addition of 20 mg of AIBN, the reaction mixture was further stirred for three hours at 60° C. The subsequent distillation under reduced pressure gave 0.30 g of (S)-(−)-1-(pentafluorophenyl)ethanol.

Example 13

To an ice-cooled solution of 0.21 g (1 mmol) of (S)-(−)-1-(pentafluorophenyl)ethanol and 0.17 g (1.5 mmol) of methanesulfonyl chloride in 2 m( of ether, was added dropwise 0.22 m( (1.6 mmol) of triethylamine. After it was stirring for two hours at room temperature, 1N hydrochloric acid was added to the reaction mixture and was extracted with ether. This ether solution was washed with 1N hydrochloric acid and an aqueous solution of 5 wt% potassium carbonate, and the solvent was distilled off under reduced pressure. The subsequent distillation gave 0.24 g (yield: 83%) of (S)-(−)-1-(pentafluorophenyl)ethyl methanesulfonate having the aforementioned physical properties.

Reference Example 3

A mixture of 1.50 g 10 mmol) of (R)-(−)-2-phenylpropionic acid and 1.43 g (12 mmol) of thionyl chloride was stirred for two hours at 60° C., and excess thionyl chloride was distilled off under reduced pressure, thereby obtaining 1.60 g (95%) of a crude product of (S)-(2)-phenylpropionyl chloride. To an ice-cooled solution of 0.42 g (2 mmol) of (S)-(−)-1-(pentafluorophenyl)ethanol and 0.79 g (10 mmol) of pyridine in 5 ml of dicholoromethane, was added 0.42 g (2.5 mmol) of the aforementioned (S)-2-phenylpropionyl chloride, and was stirred overnight at room temperature. To the reaction mixture, 1N hydrochloric acid was added and extracted with ether. The extract was washed consecutively with 1N hydrochloric acid, an aqueous solution of 5 wt% potassium carbonate, and water, and was dried over magnesium sulfate. The solvent was distilled off under reduced pressure, thereby obtaining 0.65 g (94%) of (S)-(1)-(pentafluorophenyl)ethyl (R)-2-phenylpropionate. As for this product, diastereomers were separated by gas chromatography (SE-30, 2m), and its stereochemical purity was 87%de.

Reference Example 4

(S)-1-(pentafluorophenyl)ethyl (S)-2-phenylpropionate was obtained in an operation similar to that of Reference Example 3, using (S)-(+)-2-phenylpropionic acid as a starting material. As for this product, diastereomers were separated by gas chromatography (SE-30, 2m), and its stereochemical purity was 92%de.

Example 14

A mixture of 3.3 mg (22 μmol) of (S) +)-2-phenyl-propionic acid, 29 mg (100 μmol) of (S)-(−)-1-(pentafluorophenyl)ethyl methanesulfonate, 0.5 ml (500 μmol) of an aqueous solution of 1N sodium hydroxide, 0.17 g (500 μmol) of tetrabutylammonium hydrogen sulfate, and 0.5 ml of dichloromethan was shaken vigorously for two minutes at room temperature. The dichloromethane layer was analized by gas chromatography (SE-30, 2m) and was compared with Reference Examples 3 and 4. Consequently, (R)-(1)-(pentafluorophenyl)ethyl (S)-2-phenylpropionate (yield: 90% according to the calibration curve) was detected with 80%de.

Example 15

When an operation was carried out in the same manner as that of Example 14 by starting with (±)-2-phenylpropionic acid, the stereochemical purity of the ester produced was 0%de, and no kinetic resolution had occurred.

Accordingly, it is apparent that the optically active 1-(pentafluorophenyl)ether sulfonate can be used for determination of the optical purity of chiral carboxylic acid.

Example 16

A Teflon vessel containing 2.7 g (22.5 mmol) of diisopropylamine was cooled in a dry-ice methanol bath, and to this was added dropwise 1.8 g (90 mmol) of anhydrous hydrogen fluoride to prepare 4.5 g (22.5 mmol) of (i-Pr)$_2$NH . 4HF. To this was added dropwise 3.15 g (15 mmol) of (+)-pentafluorostyrene oxide at 0° C. and the resulted mixture was stirred for 30 hours under N$_2$ at room temperature. To this was added 30 ml of diethyl ether and 30 ml of water and the aqueous layer was extracted with 20 ml of ether. The combined ether solution was washed with an aqueous solution of sodium carbonate and then water, and was dried over anhydrous sodium sulfate. After ether was distilled off, distillation under reduced pressure was carried out (Kugelrohr, 70–80° C./15 mmHg), thereby obtaining 1.0 g of (+)-2-fluoro-2-(pentafluorophenyl)ethanol. The yield was 29%, the GC purity was 98%, and $[\alpha]_D^{25}$ was +12.0° (c=0.30, CHCl$_3$). The other physical properties were mentioned above.

Example 17

To Teflon vessel containing 4.2 g (22.5 mmol) of tributylamine was cooled in a dry-ice methanol bath, and to this was added dropwise 2.3 g (112.5 mmol) of anhydrous hydrogen fluoride to prepare 6.4 g (22.5 mmol) of n-Bu$_3$N.5HF. To this was added dropwise 3.15 g (15 mmol) of (+)-pentafluorostyrene oxide at 0° C., and was stirred for 10 hours at 40° C. After it was left to cool, the same treatment as that provided in Example 16 gave 1.1 g of (+)-2-fluoro-2-(pentafluorophenyl)ethanol. Its GC purity was 96%, while its $[\alpha]_D^{25}$ was +10.8° (c=0.54, CHCl$_3$).

Example 18

To a polyethylene vessel containing 2.58 g (9.8 mmol) of a pyridine-hydrogen fluoride complex (30/70 W/W%, made by Aldrich) was added dropwise 3.15 g (15 mmol) of (+)-pentafluorostyrene oxide on an ice bath, and was stirred for 30 minutes. The same treatment as that provided in Example 16 gave 1.25 g of (+)-2-fluoro-2-(pentafluorophenyl)-ethanol. Its GC purity was 96%, while its $[\alpha]_D^{25}$ was +4.1° (c=0.49, CHCl$_3$).

As described above, novel pentafluorophenyl derivatives including optically active ones in accordance with the present invention can be used very effectively as optical resolving and electron capturing agents for sensitive analysis and as intermediates for producing medicines, agricultural chemicals, and functional organic materials such as liquid crystal compounds.

In particular, the above-described derivatives can be good electron captivating agents since they have a pentafluorophenyl group. Hence, detection with an electron capture detector (ECD) or detection of M$^-$ in mass spectrometry become possible.

Also, a derivative having a sulfonyloxy group as a good leaving group can be used suitably as a derivatizing agent for carboxylic acids, alcohols, amines, thiols, etc.

In addition, the operation of the derivatization in accordance with the present invention is very simple, and can be carried out in the presence of water. Accordingly, it could be used for aqueous samples such as body fluids.

In particular, the derivatization of chiral compounds using an optically active pentafluorophenyl derivative afford the corresponding diastereomers which are separable by chromatography. Hence, the analitical method in the present invention is applicable to determination of optical purity of chiral carboxylic acids, alcohols, amines, thiols, etc.

Furthermore, the racemic and optically active pentafluorophenyl derivatives can be produced by a simple operation from racemic and optically active pentafluorostyrene oxides, respectively.

What is claimed is:

1. A method of producing 2-(pentafluorophenyl)-1-alkanols expressed by the following formula (III):

where R$^4$ represents an alkyl group having from 1 to 4 carbon atoms, comprising:
  reacting 2,3,4,5,6-pentafluorostyrene oxide with trialkylaluminum having an alkyl group of from 1 to 4 carbon atoms.

2. The method according to claim 1, wherein said 2,3,4,5,6-pentafluorostyrene oxide is optically active, said 2-(pentafluorophenyl)-1-alkanols being optically active and expressed by the following formula (IV):

where C* represents asymmetric carbon; R$^4$ represents an alkyl group having from 1 to 4 carbon atoms.

3. A method of producing 2-(pentafluorophenyl)alkanoic acids expressed by the following formula (V):

where R$^4$ represents an alkyl group having from 1 to 4 carbon atoms, comprising:

oxidizing, with an oxidizing agent, 2-(pentafluorophenyl)-1-alkanols expressed by the formula (III):

$$C_6F_5-\underset{\underset{R^4}{|}}{CH}-CH_2OH \qquad (III)$$

where $R^4$ represents an alkyl group having from 1 to 4 carbon atoms.

4. The method according to claim 3 wherein said 2-(pentafluorophenyl)-1-alkanols are optically active and expressed by the following formula (IV):

$$C_6F_5-\underset{\underset{R^4}{|}}{C^*H}-CH_2OH \qquad (IV)$$

where C* represents asymmetric carbon; $R^4$ represents an alkyl group having from 1 to 4 carbon atoms, said 2-(pentafluorophenyl)-1-alkanoic acids being optically active and expressed by the formula (VI):

$$C_6F_5-\underset{\underset{R^4}{|}}{C^*H}-COOH \qquad (VI)$$

where C* represents asymmetric carbon; $R^4$ represents an alkyl group having from 1 to 4 carbon atoms.

5. A method of producing 2-(pentafluorophenyl)alknoil chlorides expressed by the following formula (VII):

$$C_6F_5-\underset{\underset{R^4}{|}}{CH}-COCl \qquad (VII)$$

where $R^4$ represents an alkyl group having from 1 to 4 carbon atoms, comprising:

reacting, with a chlorinating agent, 2-(pentafluorophenyl)-alkanoic acids expressed by the formula (V):

$$C_6F_5-\underset{\underset{R^4}{|}}{CH}-COOH \qquad (V)$$

where $R^4$ represents an alkyl group having from 1 to 4 carbon atoms.

6. The method according to claim 5 wherein said 2-(pentafluorophenyl)alkanoic acids are optically active and expressed by the following formula (VI):

$$C_6F_5-\underset{\underset{R^4}{|}}{C^*H}-COOH \qquad (VI)$$

where C* represents asymmetric carbon; $R^4$ represents an alkyl group having from 1 to 4 carbon atoms, said 2-(pentafluorophenyl)alkanoil chlorides being optically active and expressed by the following formula (VIII):

$$C_6F_5-\underset{\underset{R^4}{|}}{C^*H}-COCl \qquad (VIII)$$

where C* represents asymmetric carbon; $R^4$ represents an alkyl group having from 1 to 4 carbon atoms.

7. A method of producing 2-fluoro-2-(pentafluorophenyl)-ethanol expressed by the following formula (XVII):

$$C_6F_5-\underset{\underset{F}{|}}{CH}-CH_2OH \qquad (XVII)$$

comprising;

reacting 2,3,4,5,6-pentafluorostyrene oxide with an amine-hydrogen fluoride complex.

8. The method according to claim 7, wherein said 2,3,4,5,6-pentafluorostyrene oxide is optically active, said 2-fluoro-2-(pentafluorophenyl)ethanol being optically active.

9. A method of producing 2-(pentafluorophenyl)alkane amides expressed by the following formula (X):

$$C_6F_5-\underset{\underset{R^4}{|}}{C^*H}-COCl \qquad (VIII)$$

wherein $R^1$ and $R^2$ are selected from the group of alkyl, substituted alkyl, aryl, substituted aryl and hydrogen; and $R^4$ represents an alkyl group having from 1 to 4 carbon atoms;

the method comprising:

reacting 2-(pentafluorophenyl)alkanoyl chlorides expressed by the formula (VII):

$$C_6F_5-\underset{\underset{R^4}{|}}{CH}-COCl \qquad (VII)$$

wherein $R^4$ represents an alkyl group having from 1 to 4 carbon atoms, with amines expressed by the formula (IX):

$$NHR^1R^2 \qquad (IX)$$

wherein $R^1$ and $R^2$ are selected from the group of alkyl, substituted alkyl, aryl, substituted aryl, and hydrogen.

10. The method according to claim 9 wherein said 2-(pentafluorophenyl)alkanoyl chlorides are optically active and expressed by the following formula (VIII):

$$C_6F_5-\underset{\underset{R^4}{|}}{C^*H}-COCl \qquad (VIII)$$

wherein

C* represents asymmetric carbon; $R^4$ represents an alkyl group having from 1 to 4 carbon atoms; said 2-(pentafluorophenyl)alkane amides expressed by the following formula (XI):

$$C_6F_5-\underset{\underset{R^4}{|}}{C^*H}-CONR^1R^2 \qquad (XI)$$

wherein

C* represents asymmetric carbon;

$R^1$ and $R^2$ are selected from alkyl, substituted alkyl, aryl, substituted aryl, and hydrogen; and $R^4$ represents an alkyl group having from 1 to 4 carbon atoms.

11. A method of producing an optically active pentafluorophenyl derivative expressed by the following formula (XII):

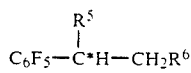  (XII)

wherein
R⁵ and R⁶ are selected from hydrogen and hydroxyl, and are different from each other; and
C* represents asymmetric carbon; the method comprising:
reacting an optically active 2,3,4,5,6-pentafluorostyrene oxide with a compound expressed by the formula Li₂MX₄, wherein M represents a copper or nickel atom, and X represents a halogen atom.

12. A method of producing optically active 1-(pentafluorophenyl)ethanols, comprising:
reacting optically active 2-halo-1-(pentafluorophenyl)ethanols expressed by the following formula (XIII) wherein R⁷ represents a halogen atom:

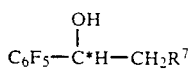  (XIII)

with an organotin hydride expressed by the formula R₄₋ₙSnHₙ, wherein each R is independently selected from alkyl groups having from 1 to 7 carbon atoms, and n is 1 or 2.

13. A method of producing 1-(pentafluorophenyl)ethyl sulfonate expressed by the following formula (XV):

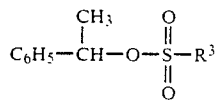  (XV)

wherein R³ is selected from alkyl, substituted alkyl, aryl, and substituted aryl, comprising:
reacting 1-(pentafluorophenyl)ethanol with sulfonyl chloride expressed by the formula (XIV):

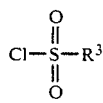  (XIV)

where R³ is selected from alkyl, substituted alkyl, aryl and substituted aryl.

14. The method according to claim 13 wherein said 1-(pentafluorophenyl)ethanol is optically active, said 1-(pentafluorophenyl)ethyl sulfonate being optically active and expressed by the following formula (XVI):

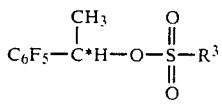  (XVI)

wherein C* represents asymmetric carbon, and R³ is selected from alkyl, substituted alkyl, aryl and substituted aryl.

15. A method of optical resolution of carboxylic acid, comprising:
reacting chiral carboxylic acids with an optically active 1-(pentafluorophenyl)ethyl sulfonate expressed by the following formula (SVI):

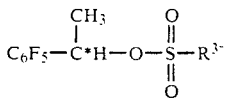  (XVI)

wherein C* represents asymmetric carbon, and R³ is selected from alkyl, substituted alkyl, aryl and substituted aryl.

16. Pentafluorophenyl derivatives expressed by the following formula (I):

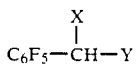  (I)

wherein
X is a halogen;
Y is selected from the group of
—CH₂OH,
—COOH,
—COCl, and
—CONR¹R²;
R¹ and R² are selected from the group of alkyl, substituted alkyl, aryl, substituted aryl and hydrogen.

17. Pentafluorophenyl derivatives expressed by the following formula (I):

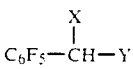  (I)

wherein
X is selected from an alkyl group having from 1 to 4 carbon atoms;
Y is selected from the group of
—COOH,
—COCl,
—CONR¹R² and
—OSO₂R³;
R¹, R² and R³ are selected from the group of alkyl, substituted alkyl, aryl, substituted aryl and hydrogen;
provided, R³ may not be hydrogen.

18. Optically active pentafluorophenyl derivatives expressed by the following formula (II):

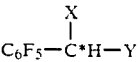  (II)

wherein
C* represents asymmetric carbon;
X is hydroxyl or a halogen;
Y is selected from the group of
—CH₂OH,
—COOH,
—COCl,
—CONR¹R²,
—OSO₂R³ and
—CH₂Y';
R¹, R² and R³ are selected from the group of alkyl, substituted alkyl, aryl, substituted aryl and hydrogen; and
Y' is halogen;

provided,

R³ may not be hydrogen;

when X is hydroxyl, Y is —CH₂Y'; and when X is halogen, Y is other than CH₂Y' or —OSO₂R³.

19. Optically active pentafluorophenyl derivatives expressed by the following formula (II):

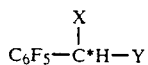
$$C_6F_5-\overset{X}{\underset{|}{C^*H}}-Y \qquad (II)$$

wherein

C* represents asymmetric carbon;

X is an alkyl group having from 1 to 4 carbon atoms;

Y is selected from the group of
- —COOH,
- —COCl,
- —CONR¹R²,
- —OSO₂R³ and
- —CH₂Y';

R¹, R² and R³ are selected from the group of alkyl, substituted alkyl, aryl, substituted aryl and hydrogen; and Y' is halogen;

provided, R³ may not be hydrogen.

20. A pentafluorophenyl derivative according to claim 16 wherein X is fluorine.

21. An optically active pentafluorophenyl derivative according to claim 18 wherein X is fluorine.

* * * * *

UNITED STATES PATENT AND TRADEMARK OFFICE
CERTIFICATE OF CORRECTION

PATENT NO. : 5,041,641
DATED : August 20, 1991
INVENTOR(S) : Osamu Takahashi, et al.

It is certified that error appears in the above-identified patent and that said Letters Patent is hereby corrected as shown below:

Abstract, front page, line 8: change "$CON^1R^2$" to --$CONR^1R^2$"--; Claim 5, col. 17, lines 29-30: change "alknoil" to --alkanoyl--; Claim 6, col. 17, line 60: change "alkanoil" to --alkanoyl--; Claim 9, col. 18, lines 19-21: The formula and parenthetical to the right of the formula should read as follows:

Signed and Sealed this

Ninth Day of February, 1993

Attest:

STEPHEN G. KUNIN

Attesting Officer

Acting Commissioner of Patents and Trademarks